United States Patent

Metelski et al.

[11] Patent Number: 6,162,523
[45] Date of Patent: Dec. 19, 2000

[54] SUPPORT INTENDED IN PARTICULAR FOR A SURGICAL MICROSCOPE

[75] Inventors: Andreas Metelski, Romanshorn, Switzerland; Kari-Heinz Wager, Gotzis, Austria

[73] Assignee: Leica Microsystems AG, Heerbrugg, Switzerland

[21] Appl. No.: 09/068,911

[22] PCT Filed: Nov. 27, 1996

[86] PCT No.: PCT/EP96/05241

§ 371 Date: Sep. 11, 1998

§ 102(e) Date: Sep. 11, 1998

[87] PCT Pub. No.: WO97/20166

PCT Pub. Date: Jun. 5, 1997

[30] Foreign Application Priority Data

Nov. 27, 1995 [CH] Switzerland .................. 1467/95

[51] Int. Cl.[7] .................................... B32B 5/12
[52] U.S. Cl. ................... 428/113; 428/298.1; 428/299.1; 428/299.4; 428/299.7; 428/300.7; 378/193
[58] Field of Search .................. 428/297.4, 298.1, 428/299.1, 113, 299.4, 299.7, 300.7; 378/193

[56] References Cited

U.S. PATENT DOCUMENTS

| 5,425,068 | 6/1995 | Scaefer et al. | 378/197 |
| 5,557,982 | 9/1996 | Voss et al. | 428/113 |
| 5,571,610 | 11/1996 | Loftus et al. | 428/902 |

FOREIGN PATENT DOCUMENTS

| 0 476 551 | 3/1992 | European Pat. Off. | G02B 21/24 |
| 0 476 552 | 3/1992 | European Pat. Off. | |
| 0 554 711 | 8/1993 | European Pat. Off. | A61B 19/00 |
| 0 628 290 | 12/1994 | European Pat. Off. | |
| 2 645 070 | 10/1990 | France . | |
| 33 13 155 | 10/1984 | Germany . | |
| 42 14 858 | 2/1994 | Germany . | |

*Primary Examiner*—Elizabeth M. Cole
*Attorney, Agent, or Firm*—Simpson, Simpson & Snyder, L.L.P.

[57] ABSTRACT

The invention concerns a novel support which has at least one bearing unit (1,2,4,16,40) made from a fiber-reinforced synthetic material and which is therefore light and stable and has positive optical characteristics. In a further embodiment, the invention is provided with vibration damping means between adjacent bearing elements (1,2,4,16,40) or parts of the bearing elements.

23 Claims, 2 Drawing Sheets

SUPPORT INTENDED IN PARTICULAR FOR A SURGICAL MICROSCOPE

BACKGROUND OF THE INVENTION

A. Field of the Invention

The present invention relates to the field of adjustable counterbalanced stands for supporting a load, more specifically a surgical microscope, to be selectively positioned by a user.

B. Description of the Prior Art

Surgical microscopes are being used more and more in surgery. Because of their heavy weight, they must be supported on stands. Several noted manufacturers have offered stands which meet the requirement of holding the load of the surgical microscope from the mechanical and static viewpoint. The applicant, for instance, sells stands with the designation OH, which are produced by Mitaka and other manufacturers. One example of such a stand appears in European Patent Application A-628 290. Zeiss, for example, disclosed a stand in European Patent 47 65 52. Most of the modern stands have parallelogram supports so as to be able to support the load of the surgical microscope without bending or twisting, so that the microscope will have the maximum freedom of movement and maximum radius of action.

European Patent Application A-628 290, for example, shows such a design. The design shown in FIG. 1 of that patent has a massive C-shaped base pedestal which carries a first parallelogram support, extended vertically and pivotable about a vertical pivot axis. The first parallelogram support carries a second parallelogram support extending horizontally, which can be pivoted about a first horizontal pivot axis. A connection between the two parallelogram supports with an additional pivot point on the base pedestal keeps both the vertical arms of the second parallelogram support always in the vertical position.

On the peripheral vertical arm of the second parallelogram support there is a third parallelogram support, extended horizontally, pivotable about a second horizontal pivot axis. Its peripheral vertical arm is likewise always held vertical and is connected, as a single piece, with a central vertical arm of a fourth parallelogram support which extends vertically.

A surgical microscope is mounted, so that it can be rotated or pivoted, on a lower horizontal arm of the fourth parallelogram support. With this mounting it has any desired degree of freedom so that it can be moved to a desired position by the user and held in that position. All of the parallelogram supports have relatively massive main supports and weaker secondary supports which transfer essentially only tensions or pressures. For static reasons it turns out that all the massive main supports are turned toward the space circumscribed by the stand, which is usually utilized by the user.

The main supports are bent out of their linear longitudinal extension, which is statically effective, by right-angle joints. That was desired at the state of the technology, because that was how designers attempted to keep the user's space as great as possible.

One of the ideas of the standard surgical stand manufacturers was that very massive parts and heavier counterweights improved the stability of the stand during its use.

The Contraves company also offered a similar microscope stand with two separate counterweights. One is movable in the horizontal direction on a horizontal parallel bar which transfers the balancing force, and the other is movable in the vertical direction. Such a stand is described, for instance, in the older European Patent Application B 476 551. That stand avoided right-angle joints. That caused a certain limitation of the working space for the user, as can be seen by comparing, for instance, FIG. 1 of the '551 publication with FIG. 4 of the '290 publication.

A stand according to the more recent Europe an Patent Application A-628 290 was marketed by its applicant (Mitaka) along with this applicant. That stand's advantage of gaining space was combined with disadvantages, though.

Production of the bent arms is considerably more expensive than use of straight arms. The bends in the main support produce shear-like overlaps with the secondary s upports at the ends of the parallel supports. That is best seen from FIGS. 1–6 of the European Patent Application. The se overlaps conceal a certain disadvantage, especially for inexperienced operating personnel, because if the personnel are not careful, cables, items of clothing, objects, or even arms or legs can get caught. That is particularly true for the region immediately around the load , e.g., the microscope, as that is where the user generally does most of his direct work.

SUMMARY OF THE INVENTION

In this invention, the applicant proceeded anew on the thesis, according to the invention, that even light microscopes can have good stability if they are designed with different parts. Significant advantages over the known massive stands would be better transportability and broader usability (fewer problems with the load-bearing capacity of the floor, etc.) Alternatively, it should be able to achieve greater a greater radius of action for the user with the same weight.

The invention is based on those objectives, as well as on the desire to simplify production. Thus, for instance, longer straight arms (without bends) should replace the bent ones, which are heavier and thus rather short so as to attain the same free space for the user without bending (which adds to the cost of production).

On the other hand, the new design according to the invention should not make the movement geometry, which is already adequate at the state of the technology, any poorer.

The supports to be used according to the invention, which, if necessary, can be used in frameworks of parallelogram supports, should as much as possible be straight, simple parts.

In attaining these objectives, the applicant has provided a stand which uses at least one support made of a fiber-reinforced composite material, preferably plastic.

Based on the concept of replacing the usual parallel arms by fiber-reinforced plastic elements, particularly tubes, according to the invention, weight can be saved while the strength or the radius of action is simultaneously increased. That makes the stand lighter. This effect is detectably increased by the fact that, because the weight of the support itself, as well as the weight of the load, must be compensated by balancing weights, the weight of the support can be reduced by reducing the weight of the arm.

A stand according to the invention thus becomes more easily transportable and also attains the other objectives pointed out initially.

Preferred embodiments use, as the plastic, thermoplastics, thermosetting resins (epoxy resins) or a mixture of them. Preferred fibers include carbon fibers, aramid fibers, glass or mineral fibers, polyamide fibers, or a mixture of those.

In this respect, explicit reference is made to the earlier Swiss Patent Application by the applicant, "m.Z. P3531CH of Oct. 12, 1995", in which aspects of this invention have previously been mentioned. Both applications, along with the Swiss Patent Application "m.Z. P3623CH" submitted on the same date as this application, describe an entirely new microscope with several inventions and desirable variants. These patents are expressly referred to here and their contents are considered disclosed herein for the purpose of a later combination of the teachings of these three applications with a favorable priority.

This invention is not, however, limited to use in conjunction with the teachings of the Swiss applications cited. Instead, it can also be used in other stands, such as in robotics or astronomy.

According to a further development of the invention, the mechanical and dynamic properties of the supports can be influenced by intentional adjustment of the fiber orientation. For instance, various methods for winding the fibers or layers of the support can be used: filament winding, braided tube, cloth and layers, which may be laid or oriented unidirectionally or at special angles. For instance, in one actual embodiment, the vertical main base which holds the main support of the stand, is laid with an isotropic layer such that if the tube direction=0°, the direction of the layers is ± about 45° or at less acute angles, e.g., 0, ±45–55°, which gives a particularly high torsional stiffness that is advantageous, as high torsional moments can occur when the stand is locked to the base, as in the case of a horizontal impact near the load mount, or if the brakes are applied while the microscope is being moved. With the preferred use of carbon fibers with thermosetting resin, the main base is preferably made of a tube 10 cm in diameter and 4 mm thick, with fibers crossed at the angle mentioned, with a fiber weight of about 130–160 g/m$^2$. It is particularly preferred for the angle to be slightly variable, so that layers at essentially the same angle support each other. For example, for a desired direction of 55°, one layer is laid at 50° and then a second is laid at 60°, giving, on the average, a direction of 55°. That improves the ultimate strength of the support. This latter type of winding is, of course, also helpful for the other supports of the stand, even though a more acute angle is preferred for the other supports, e.g., 0, ±(15–25°) to (±30–40°), as these tubes are more severely stressed in tension/pressure and bending.

Thus the invention offers particularly suitable mechanical parts tailored for the components required geometrically, with lower weight and higher strength. Other special developments and variants of them are described in the patent claims.

If the supports are made of carbon-fiber-reinforced thermosetting resin, there is another outstanding effect compared with the known ones, especially if the supports (tubes) are ground, polished, and varnished. The structure of the carbon fibers, visible under the varnish, gives color effects and a strikingly improved appearance over those used in the past. That is desirable and advantageous in improving the appearance of operating rooms.

Use of about 10 parts by weight of blue varnish with about 90 parts by weight clear varnish is particularly pleasing visually. The varnish is preferably sprayed on, or applied by dipping. Carbon-fiber-reinforced tubes made, according to one example embodiment, by means of inflation technology, stretched-film winding, or autoclaving, are, after curing, prepared for finishing by light grinding using about 300–400 grit (e.g., according to DIN 69100). That is followed by a polishing agent such as M-Scotch-Brite 7448 (trademark of the 3M company), with the grinding and polishing preferably carried out in the fiber direction. Then, after thorough cleaning, the varnish mixture noted is sprayed on and the tube is finished by drying. A second similar coat of varnish can be applied in the wet-wet process for better depth effect. The visually pleasing translucence effect can be influenced by changing the proportion of the colored varnish. More than 10% by weight colored varnish gives less translucence, and less than 10% colored varnish gives more translucence. That can be increased to give a "glass-clear" effect. In the example used, two-component epoxy varnish was used for a good visual effect.

The fiber-reinforced tubes or supports can be bonded to the other parts by means of a metallic interface which can, for example, be fastened to the tube or support by screws or pins, or by cementing.

Another measure that can be used independently of that above is used according to the invention to damp vibrations that may occur in the mechanical structure, thus achieving better operating safety: According to this special embodiment of the invention, at least one interface between two load-bearing parts of the stand is kept free of stress. That can be done, in the simplest case, by loosening the connection between these two parts (e.g., a screw connection) so that vibrations cannot be transferred, but the parts cannot separate from each other.

Additional damping effects can be achieved if damping materials are used as intermediate layers at the appropriate interfaces.

A significant effect according to the invention is that this measure prevents vibrations caused by minor impacts or changes of position from passing through the whole stand, perhaps being reflected back from the mounting surface (floor or ceiling, for example) and getting to the microscope.

The preferred locations for the stress-free separation are those placed on the stand at which balanced equilibrium prevails, so that hardly any bending stresses occur. In one example embodiment, the position immediately below the main bearing in the pedestal is provided as such a point, as the stand above the main bearing is in a balanced state if it is built according to the application "m.Z. P3531CH".

Other areas for releasing stress and/or insertion of damping materials are, if desired, also between the bearing points for the wheels, mounting feet, or the like, and the other parts of the stand.

If necessary, the designs according to the invention can be made even lighter than previous metal designs with motorized positioning drives which make possible automatic adjustment of the support arm slopes if necessary, as in bringing the stand into a preselected position by remote control. Obviously, full automation still requires position or movement sensors acting as references for the required drives. On the other hand, according to one particular embodiment of the invention, such drives can also operate as stepping motors with integrated sensors, so that drive and measurement occur in the same step. In further progression, it is possible in this way to achieve completely independently positionable stands which, in contrast to those now known (e.g., from European Patent Application A-554 711 by the Carl Zeiss company) use elegant, light-weight supporting elements and are of correspondingly light construction.

In the course of automatic balancing, it is particularly helpful to have the vibration damping according to the invention because then measurements of the state of balancing are not affected and the balancing goes faster. The speed can be increased because of the reduced mass and thus the reduced inertia.

Another advantage from use of the new kind of fiber-reinforced supports in tubular form is that electrical lines and/or liquid or gas lines can be run through the inside of the tube, saving space and giving an integrated structure which can also be sterilized better.

Another further development provides coverings for joints and exposed parts of the stand. They are made of polyurethane integral form, as mentioned in the application "m.Z.P3531CH" or, alternatively, of ABS plastic, which can be foamed, if desired. These covers, along with the new kind of support materials give a more user-friendly appearance. They do not have the cold metallic feel when touched by the operating personnel, and are still protected from impact in the covered areas.

BRIEF DESCRIPTION OF THE DRAWINGS

The figures are described together. The description by figures and the reference symbol list make up a unit supplemented by the other parts of the description and claims in the sense of a complete disclosure. Identical reference symbols denote identical parts. Identical reference symbols with different indices denote similar parts with the same function. The figures are presented only as examples and are not necessarily in correct proportions. The list of figures, with the list of figures in "m.Z. P3531CH" cited above and with that of "m.Z. P3623CH" make up a unit and, in case the features of the three applications are combined, they should be read together, as should the accompanying descriptions.

DETAILED DESCRIPTION OF THE PREFERRED EMBODIMENTS

Figure 1:
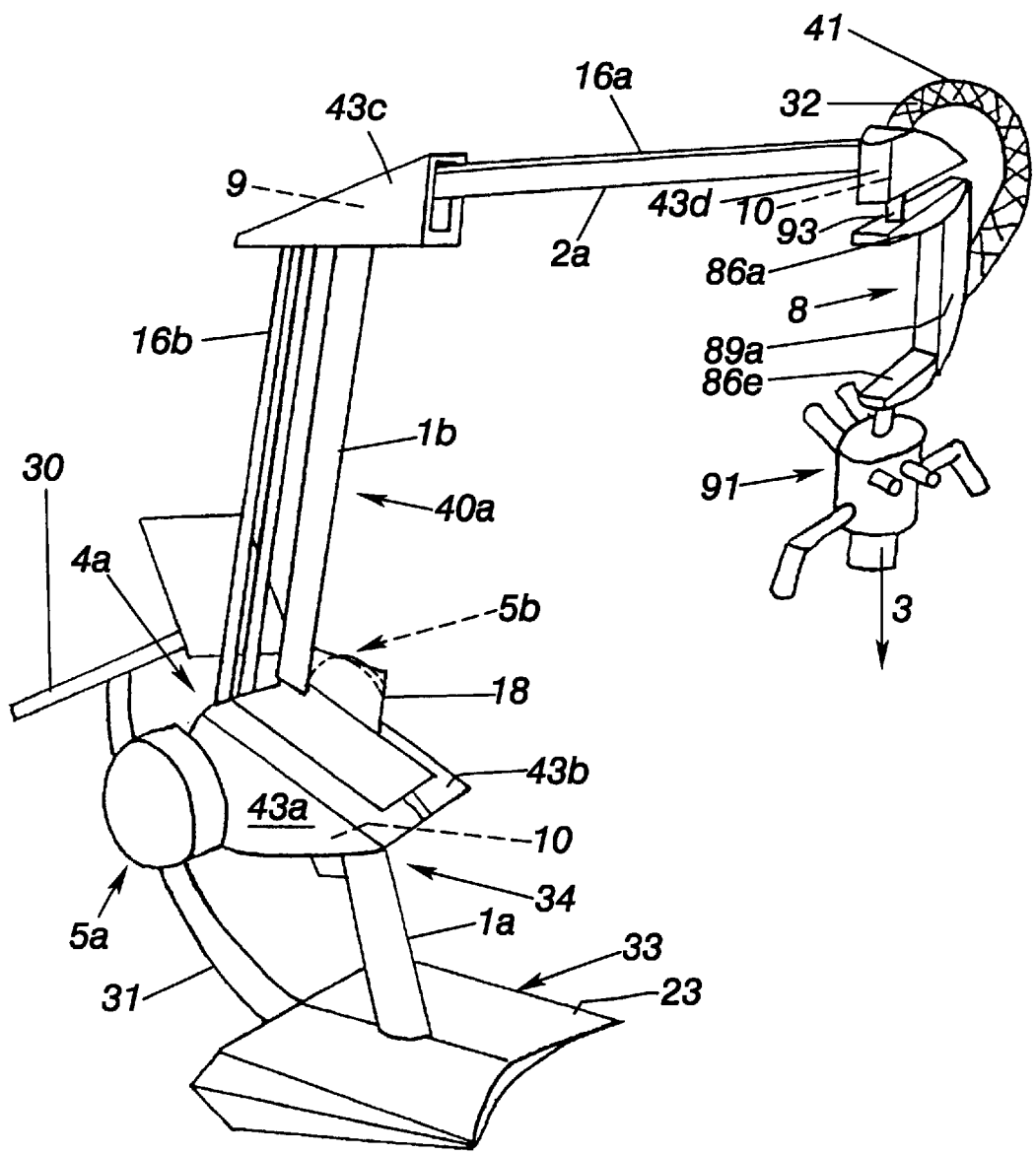
FIG. 1 shows a design view of a stand according to the invention with fiber-reinforced supports and pedestal according to the invention.
Figure 2:
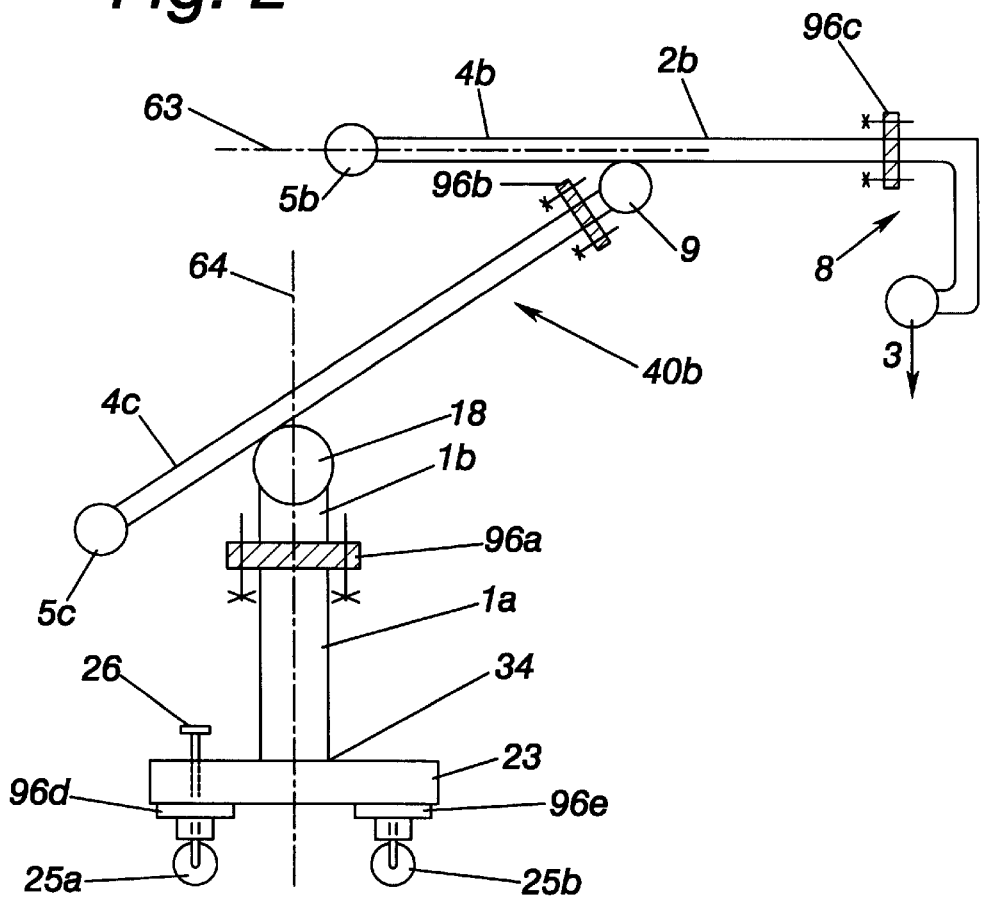
FIG. 2 is a symbolic representation of a new kind of stand with a zone of stress-free separation.

Attention is directed initially to FIGS. 1 and 2. A stand base 23 carries a pedestal 1a which supports the main bearing 18. Pedestal 1a. which can preferably be rolled over the floor, is shown only symbolically with a straight bar, but could also be C-shaped, box-shaped, or of comparable design, and does not necessarily have to serve for mounting or erecting on the floor, but could also be inverted and mounted on a ceiling, other surfaces, or furniture, movably if desired. Pedestal 1a includes a rotating bearing 34. Wheels 25a,b provided for base 23 can be fixed for travel in one preferred direction of transport or they can swivel. They can also preferably be raised or drawn up into the base by parallel adjusting feet or a positioning screw 26, so that the base can be set down on the floor. Base 23 preferably is enclosed by a housing 33 of cast material or the like, preferably coated in plastic, to lower the center of gravity of the stand. In the alternative, housing 33 can be made of plastic. A transport handle 30 with a special handlebar 31 is provided to push or pull the stand in a preferred direction of transport.

The jointed places of the stand are covered by caps 43a–d, preferably of integral foam with closed cells at all sides. Caps 43a–d prevent injuries or damages in case of collisions, and are easily removable for servicing. Other advantages which must be emphasized are low weight and the ability to produce any desired shape, thus giving the stand a pleasing appearance at low cost.

As shown in FIG. 2 the pedestal is in two parts and has an interface 96a. Here, for example, it is shown as a flange. It divides the pedestal into two parts, 1a and 1b. Pedestal head 1b terminates the pedestal at the top for holding the pivotable parts of the stand and which, in particular, sits on the pedestal 1a so that it can rotate. It could involve a bearing bracket for the bearing 18 mounted on the pedestal 1a, so that an interface is produced between it and the pedestal 1a. An important feature of the interface is that it transfers no significant stress in the vertical direction or in the direction of the stand extension. For instance, the bolts shown symbolically there are not tightened. That plays very little part with respect to the design for strength, as the entire stand is in any case balanced above bearing 18, so that there are practically no bending forces at the interface 96a.

Comparable interfaces, 96b–e, can also be established at other places within the framework of the invention. To the extent possible, they prevent vibrations being conducted past them. Vibration-damping interlayers could also be installed in areas with bending stress, such as 96b,c. Their function is to destroy mechanical vibrations, or to convert them into heat. For example, interfaces 96a–e can include elastomeric rubber with high conversion of kinetic energy into heat.

The supports 1a, 1b, 2a, 2b, 4a–4c, 16a, 16b, 40a, and 40b are preferably made of fiber-reinforced plastic, for example a fiber-reinforced composite material which comprises a mixture of a thermoplastic and a thermosetting resin, and are consequently particularly light, so that the counterweights 5a, 5b can also be light, and the weight of the entire structure is reduced from that of the usual structures. Load arms 2a, 2b and balancing arms 4a–4c may be constructed of several rods, for instance, one or more parallelogram guides. Supports 16a and 16b are horizontal and vertical tension arms, respectively. Support 40a (or support 40b in FIG. 2) is an upper tilting portion of pedestal 1a which is vertical in its resting state. It carries a horizontal pivot bearing 9 or holds it elevated. Its function is to hold the pivot bearing in case of pivoting out of a vertical plane 64, and so to move the load arm members 2a, 2b laterally so that the load 3 can be moved toward and away from the vertical plane 64. It has a vertical extension below the vertical pivot bearing 18 which acts as a balancing arm and which holds the counterweight 5b.

The stand supports a load 3, such as a microscope or any part which must be held on a stand, such as a robot arm, telescope, or the like. Movable counterweights 5a–5c can be in one piece or, particularly, divided. One of the various aspects of the invention is that two separate balancing weights swing about a vertical plane 64 and a horizontal plane 63 for two balancing functions with separate motions.

A load mount 8 includes means for mounting a microscope or other load 3. In particular, the load mounting according to a further development of the invention also includes its own balancing system, corresponding to the balancing system of the stand itself, with load and balancing arms as well as measuring means and counterweights. Load mount 8 is shown as including upper and lower horizontal arms 86a, 86e and a vertical support 89a with chain or belt drive. The chain drive or belt drive could also be replaced, within the range of the invention, by a shaft drive with universal joints and corresponding bevel gears in a way and manner which is itself known. Load 3 is mounted at an end 91 of lower horizontal support 86e, and a bearing 93 is provided for the load mount 8. An electrical or optical supply line 32 or the like is for functions of the stand, such as braking, or supplying power to the load 3 (microscope). Supply line 32 is held and protected by a tube 41—preferably a corrugated tube.

Load arms 2a, 2b and balancing arms 4a–4c pivot about a pivot axis defined by pivot bearing 9 out of a horizontal plane 63.

Figure 3:
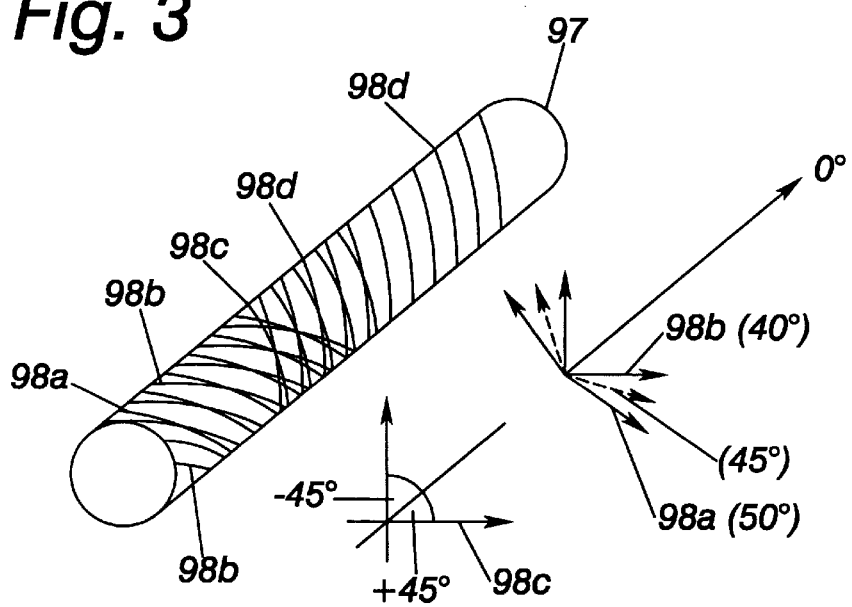
FIG. 3 is a symbolic representation of a tubular stand support according to the invention showing the fiber orientation, a detail of a structure according to FIG. 1 in section.

FIG. 3 shows symbolically how the fibers 98, which can be carbon, aramid, glass, mineral or polyamide fibers or a mixture thereof, are oriented in the example with respect to a longitudinal axis of tube 97. Four layers of fibers have angles varying from ±40°–50° to 0° (the direction of the tube 97, which is used as a support) Adjacent layer angles (40°, 50°) give an effective angle of 45° (98c). That is important to produce stiffness in torsion or bending. Such small differences in the angle, though, somewhat increase the ultimate strength as compared with a single-layer winding (for instance, only 45°), as the adjacent fibers apparently block the otherwise preferred fracture direction along the layer of winding. The supports 1a,1b making up the pedestal preferably have the following fiber orientation: 0° (tube direction) + (30°–60°), while the supports loaded in bending, such as supports 2a, 2b, 4a–4c, 16, 40a, and 40b, have the following fiber orientation: 0° (tube direction) + (10°–30°). In case of crossed angled layers the directions of the fibers 98 in each pair of layers are at a small angle (e.g., about 1°–29°) with each other, while at least one, and preferably two, other layers enclose a greater angle from the two initial angled layers (e.g., about 30°–150°).

The brake (10) and the measuring means according to the invention correspond, for example, to the detail drawing in FIGS. 18 and 19 of "m.Z. 3531CH", but the invention is not limited to that.

Use of the new stand is not limited to microscopy. Such use also covers the optical area, close-up and distant magnifications, as well as robotics and the like.

What is claimed is:

1. In a surgical microscope stand comprising a plurality of connected elongated support arms, the improvement comprising: at least one of said plurality of support arms being made of a fiber-reinforced composite material, wherein said at least one support arm includes an interface dividing said at least one support arm into two adjacent parts connected by said interface, and said interface prevents transfer of stresses from one of said two adjacent parts to another of said two adjacent parts.

2. The improvement according to claim 1, wherein said composite material includes a thermoplastic.

3. The improvement according to claim 1, wherein said composite material includes a thermosetting resin.

4. The improvement according to claim 1, wherein said composite material includes a mixture of a thermoplastic and a thermosetting resin.

5. The improvement according to claim 2, wherein said composite material is reinforced with at least one fiber component selected from the group consisting of carbon fibers, aramid fibers, glass fibers, mineral fibers, and polyamide fibers.

6. The improvement according to claim 3, wherein said composite material is reinforced with at least one fiber component selected from the group consisting of carbon fibers, aramid fibers, glass fibers, mineral fibers, and polyamide fibers.

7. The improvement according to claim 4, wherein said composite material is reinforced with at least one fiber component selected from the group consisting of carbon fibers, aramid fibers, glass fibers, mineral fibers, and polyamide fibers.

8. The improvement according to claim 1, wherein said at least one support arm extends along a longitudinal axis, and said fibers are orientated with respect to said longitudinal axis.

9. The improvement according to claim 8, wherein said longitudinal axis i s normally vertical, and a difference in orientation angle between said fibers and said longitudinal axis is from 30° to 60°.

10. The improvement according to claim 8, wherein said longitudinal axis is non-vertical and said at least one support arm is subject to a bending load, and a difference in orientation angle between said fibers and said longitudinal axis is from 10° to 30°.

11. The improvement according to claim 8, wherein said fibers are contained in at least three different layers of said support arm, a difference in orientation angle between fibers in a first of said at least three layers and fibers in a second of said at least three layers is from 1° to 29°, and a difference in orientation angle between fibers in a third of said at least three layers and fibers in said first and second of said at least three layers is from 30° to 150°.

12. The improvement according to claim 11, further including a fourth layer containing fibers having a difference in angle of orientation of from 1° to 29° with respect to fibers in said third layer.

13. The improvement according to claim 8, wherein said fibers are orientated by a filament winding process.

14. The improvement according to claim 8, wherein said fibers a reorientated by a braided tube process .

15. The improvement according to claim 8, wherein said fibers are orientated by a cloth and layers process.

16. The improvement according to claim 1, wherein said fiber-reinforced composite material is ground.

17. The improvement according to claim 16, wherein said fiber-reinforced composite material is polished.

18. The improvement according to claim 17, wherein said fiber-reinforced composite material is coated with varnish.

19. The improvement according to claim 18, wherein said varnish is a mixture of colored varnish and clear varnish.

20. The improvement according to claim 19, wherein said mixture of varnish comprises 90% by weight of clear and 10% by weight colored varnish.

21. The improvement according to claim 1, wherein said interface includes a damping interlayer for reducing the transfer of vibration energy between said two adjacent parts.

22. The improvement according to claim 21, wherein said damping interlayer is made of an elastomeric material.

23. The improvement according to claim 1, wherein said plurality of support arms includes a pedestal extending vertically upward from a foot and a pivoted portion connected to said pedestal by a main pivot bearing, and said at least one support arm comprises said pedestal such that said interface is below said main pivot bearing.

* * * * *